US009341596B1

(12) United States Patent
Chen et al.

(10) Patent No.: US 9,341,596 B1
(45) Date of Patent: May 17, 2016

(54) ANNULAR GAS IONIZATION DELTA E-E DETECTOR

(71) Applicant: International Business Machines Corporation, Armonk, NY (US)

(72) Inventors: Liang Chen, Ninghai (CN); Michael S. Gordon, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/579,366

(22) Filed: Dec. 22, 2014

(51) Int. Cl.
*G01T 1/185* (2006.01)
*G01N 27/66* (2006.01)

(52) U.S. Cl.
CPC ..................................... *G01N 27/66* (2013.01)

(58) Field of Classification Search
CPC ....... H01J 47/02; H01J 47/005; H01J 47/004; G01T 1/185; G01T 1/2935; G01T 3/008; G01N 27/66
See application file for complete search history.

(56) References Cited

U.S. PATENT DOCUMENTS

| | | | |
|---|---|---|---|
| 4,161,655 A | 7/1979 | Cotic et al. | |
| 4,316,089 A | 2/1982 | Aoyama | |
| 4,640,729 A * | 2/1987 | Fujii et al. | 156/257 |
| 4,880,983 A | 11/1989 | Markey | |
| 4,975,648 A | 12/1990 | Lawson et al. | |
| 5,920,072 A | 7/1999 | Abdel-Rahman | |
| 6,546,070 B1 * | 4/2003 | Francke | 378/51 |
| 6,781,132 B2 * | 8/2004 | McGregor | 250/370.09 |
| 6,856,669 B2 | 2/2005 | Francke et al. | |
| 7,180,076 B2 | 2/2007 | Haverstick et al. | |
| 7,495,229 B2 * | 2/2009 | Beyerle | 250/385.1 |
| 8,453,493 B2 | 6/2013 | Wall et al. | |
| 2003/0223528 A1 * | 12/2003 | Miley et al. | 376/113 |
| 2004/0108857 A1 * | 6/2004 | Jarski et al. | 324/464 |
| 2005/0067581 A1 | 3/2005 | Berhke et al. | |
| 2006/0043279 A1 * | 3/2006 | Kudryavtsev et al. | 250/282 |
| 2008/0159476 A1 | 7/2008 | Koltick et al. | |

FOREIGN PATENT DOCUMENTS

EP 0896738 B1 6/2005
JP 52-92486 6/1987

OTHER PUBLICATIONS

Adhikari et al., "Performance of an Axial Gas Ionization Detector," IEEE Transactions on Nuclear Science, Aug. 2006, p. 2270-2275, vol. 53, No. 4.

(Continued)

*Primary Examiner* — Marcus Taningco
(74) *Attorney, Agent, or Firm* — David Zwick; Louis Percello

(57) ABSTRACT

An integrated ΔE-E ionization detector that includes an outer shell having an interior linear axis, a vacuum tube coaxial with the linear axis, and a front cathode, a center anode, and a rear anode disposed within the outer shell and around the vacuum tube. The front cathode, center anode, and rear anode are substantially planar in shape, and a ΔE detection chamber is defined by the front cathode, the center anode, the outer shell, and the vacuum tube, and an E detection chamber is defined by the rear anode, the center anode, the outer shell, and the vacuum tube. All rays defining at least one solid annular angle about the linear axis and originating from a point in front of the front cathode will intersect the front cathode, internally traverse the ΔE detection chamber, intersect the center anode, and traverse at least a portion of the E detection chamber.

11 Claims, 5 Drawing Sheets

(56) References Cited

OTHER PUBLICATIONS

Bandyopadhyaya et al., "An Axial Ionization Chamber for Heavy Ion Identification," Nuclear Instruments and Methods in Physics Research Section A: Accelerators, Spectrometers, Detectors and Associated Equipment, Jun. 1989, p. 467-469, vol. 278, Issue 2.

Jhingan et al., "Hybrid telescopes for heavy ion detection," Proceedings of the DAE Symposium on Nuclear Physics, 2011, p. 1040-1041, vol. 56.

Mallepell et al., "Annular gas ionization detector for low energy heavy ion backscattering spectrometry," Nuclear Instruments and Methods in Physics Research Section B: Beam Interactions with Materials and Atoms, Apr. 15, 2009, p. 1193-1198, vol. 267, Issue 7.

Sauli, "Principles of Operation of Multiwire Proportional and Drift Chambers," CERN European Organization for Nuclear Research, May 3, 1977, Lectures given in the Academic Training Programme of CERN 1975-1976, Geneva.

International Search Report and Written Opinion, PCT/IB2015/058920, Date of Mailing Feb. 2, 2016, 7 pages.

* cited by examiner

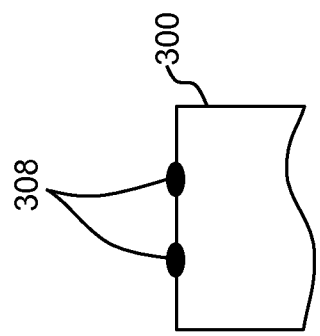
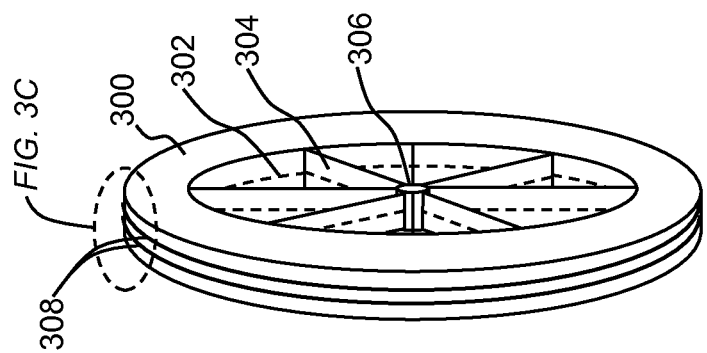
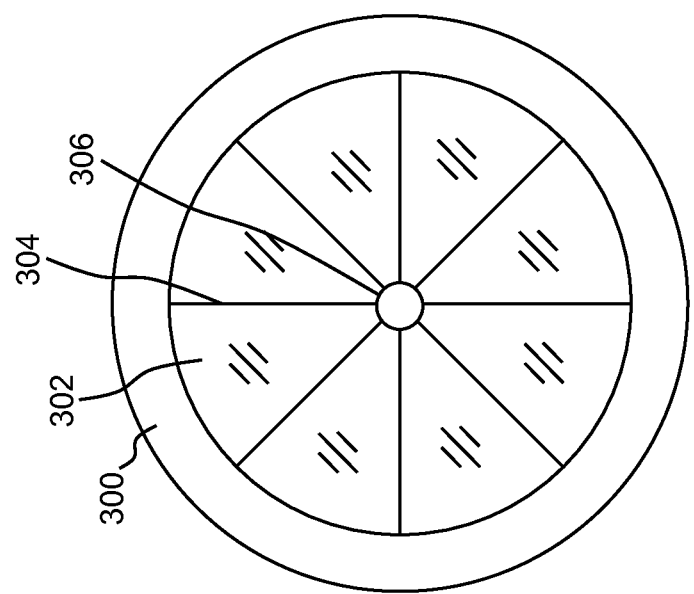
FIG. 3C
FIG. 3B
FIG. 3A

ANNULAR GAS IONIZATION DELTA E-E DETECTOR

BACKGROUND

The present invention relates generally to the field of gas ionization detectors, and more particularly to an integrated ΔE-E annular gas ionization detector.

Ion beam analysis (IBA) is a suite of analytical techniques in which a high energy ion beam is used to probe the near-surface layer of solids, such as thin films used in semiconductor fabrication, to obtain composition and, in some cases, depth profile information. Different IBA techniques are directed to varying the parameters of the beam, such as the beam energy and the incident angle of the beam with respect to the surface of the solid. The different analytical techniques may produce different interactions of the ion beam and the surface. Analyzing the interaction products may provide meaningful information about the surface layers of the solid.

One IBA technique known as Rutherford Backscattering Spectrometry (RBS) probes the surface of a target by detecting the energies of particles of the incident ion beam that are backscattered into a particle detector by atoms of the target. As is well known in the art, the energies of the backscattered particles are proportional to the mass and energy of the incident particles of the ion beam, the mass of the atoms from which the incident particles are backscattered, and the scattering angle.

With some of the IBA analytical techniques, for example, nuclear reaction analysis (NRA), the interaction of the ion beam with the surface layers may produce more than one type of particle. Distinguishing the particles may be done by determining their atomic numbers and their energies.

For measurement of the atomic number as well as the energy of energetic atoms and ions, a device commonly referred to as a ΔE-E telescope detector is often used. The ΔE-E detector includes a pair of detectors arranged so that the particles travel through a first ΔE detector and are stopped in a second E detector. The atomic number may be determined from the energy deposited by the particle within the thickness spanned by the ΔE detector, and in the E detector as the particle is stopped. The deposited energy depends on the atom number, the particle's incident energy, the gas type, and gas pressure. The total energy of the incident particle is the sum of the energy deposited in the two detectors, and energy not detected, or lost, when, for example, the particle passes through an electrically conductive window, such as a metalized Mylar film, when entering the detector, or through a dead layer in a silicon detector.

The deposited energy is typically converted into a detected electrical signal with a magnitude proportional to the deposited energy. How the deposited energy is converted into an electrical signal depends on the type of detector. Typically, almost all the energy deposited within the detectors is the result of exciting electrons of the detector material. In the case of a gas ionization detector the number of ion-electron pairs can be detected. In the case of solid detector materials, such as scintillators and semiconductors, the energy deposition typically leads to promotion of electrons across the band gap. This may cause photon emissions in the case of the scintillator, or a current pulse flowing across a junction in the case of a semiconductor detector.

SUMMARY

Embodiments of the present invention disclose an integrated ΔE-E ionization detector that includes an outer shell having an interior linear axis, a vacuum tube coaxial with the linear axis, and a front cathode, a center anode, and a rear anode disposed within the outer shell and around the vacuum tube. The front cathode, center anode, and rear anode are substantially planar in shape, and a ΔE detection chamber is defined by the front cathode, the center anode, the outer shell, and the vacuum tube, and an E detection chamber is defined by the rear anode, the center anode, the outer shell, and the vacuum tube. All rays defining at least one solid annular angle about the linear axis and originating from a point in front of the front cathode will intersect the front cathode, internally traverse the ΔE detection chamber, intersect the center anode, and traverse at least a portion of the E detection chamber.

BRIEF DESCRIPTION OF THE SEVERAL VIEWS OF THE DRAWINGS

FIGS. 3A-3C illustrate an exemplary embodiment of a cathode and/or anode structure, in accordance with an embodiment of the invention.

DETAILED DESCRIPTION

Embodiments of the invention are directed to an integrated ΔE-E annular detector 100 that includes a pair of gas ionization detectors.

Figure 1:
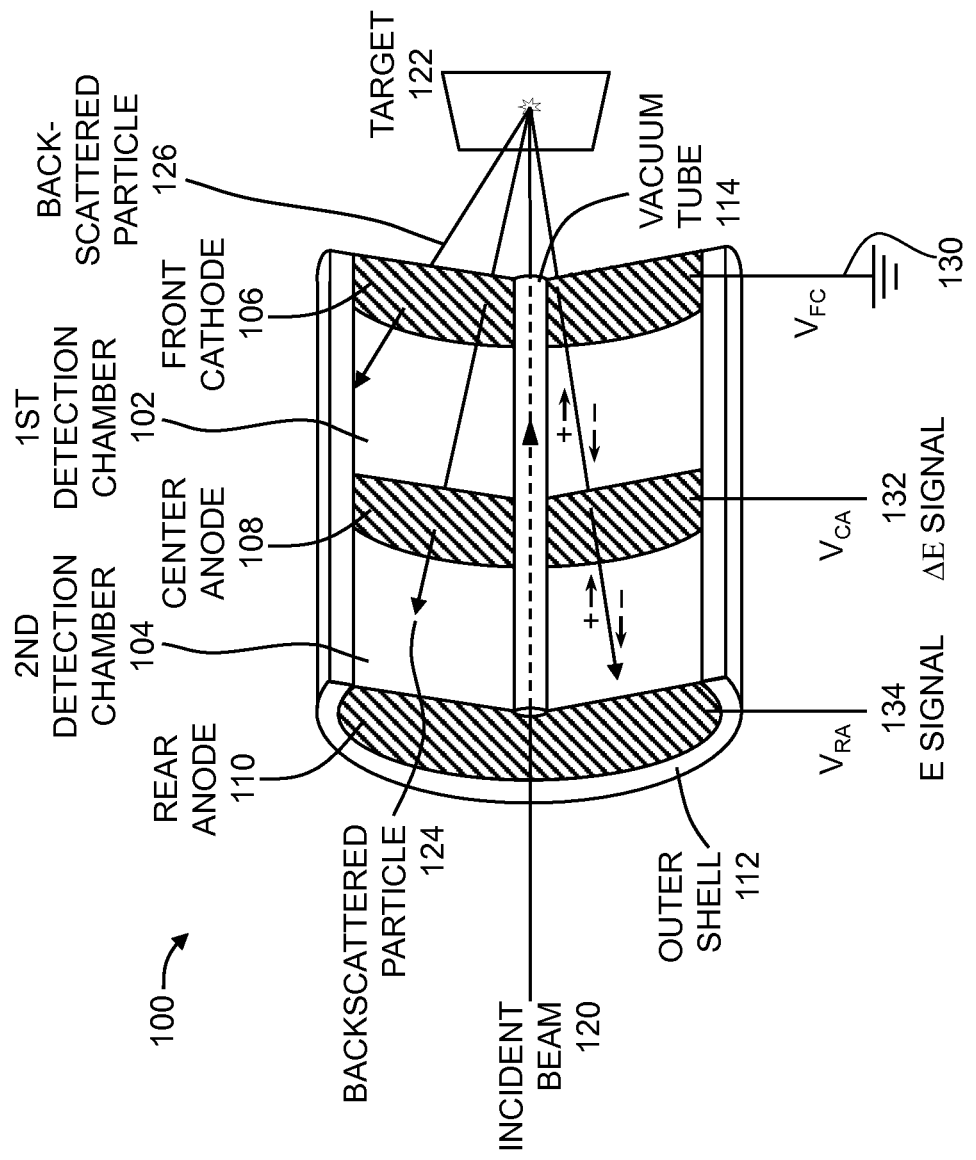
FIG. 1 is a perspective sectional view illustrating a basic arrangement of an integrated ΔE-E annular detector, in accordance with an embodiment of the present invention.

FIG. 1 is a perspective sectional view illustrating a simplified arrangement of the integrated ΔE-E annular detector 100, in accordance with an embodiment of the present invention. The integrated ΔE-E annular detector 100 includes a front cathode 106, a center anode 108, and a rear anode 110, all within a cylindrical outer shell 112. A vacuum tube 114 that is coaxial with the outer shell 112 spans at least the distance from the front cathode 106 to the rear anode 110. An annular first ionization detection chamber 102 is formed by the front cathode 106, the center anode 108, vacuum tube 114, and the outer shell 112. Similarly, an annular second ionization detection chamber 104 is formed by the rear anode 110, the center anode 108, vacuum tube 114, and the outer shell 112.

In various embodiments of the invention, first ionization detection chamber 102 and second ionization detection chamber 104 are interior volumes that are sealed with respect to each other and the environment in which the integrated ΔE-E detector 100 operates—for example, an evacuated scattering chamber. This arrangement allows for a gas within the first ionization detection chamber 102 to be maintained at a pressure different from the pressure of a gas within the second ionization detection chamber 104.

In other embodiments of the invention, first ionization detection chamber 102 and second ionization detection chamber 104, while sealed with respect to the environment in which the integrated ΔE-E detector 100 operates, are not sealed with respect to each other. In these embodiments, the gas pressures in first ionization detection chamber 102 and second ionization detection chamber 104 are the same.

Generally, front cathode 106, center anode 108, and rear anode 110 are pseudo-parallel to one another, and are pseudo-orthogonal to the axis of outer shell 112 and the vacuum tube 114. That is, for example, the circles on the interior surface of outer shell 112 defined by the anchoring positions of front cathode 106, center anode 108, and rear anode 110 are on parallel planes that are orthogonal to the axis of the outer shell 112 and vacuum tube 114. In operation, as described in more detail below, gas pressure differences between the first ionization detection chamber 102, second ionization detection chamber 104, and the vacuum of the test environment may cause front cathode 106, center anode 108, and/or rear anode 110 to distend away from a planar surface. Depending on the support structures on which the front cathode 106, center anode 108, and/or rear anode 110 are mounted, for example, a hub and spoke arrangement, the distended shapes may be rather irregular.

In certain embodiments, outer shell 112 may be other than cylindrical in shape. For example, the outer shell may be frusto-conical in shape, formed, for example, from a circular or elliptical cone. Other implementations may use other frustum shapes. In general, an outer shell having the shape of any frustum having a linear interior axis, including a cylinder, may be used provided the operation of such a ΔE-E ionization detector is in accordance with embodiments of the invention. In various embodiments, the front cathode 106, center anode 108, and/or rear anode 110 are independently axially moveable within outer shell 112, while maintaining the sealed aspects of first ionization detection chamber 102 and second ionization detection chamber 104.

In various embodiments, a voltage $V_{CA}$ is applied on center anode 108 and a voltage $V_{RA}$ is applied on rear anode 110 with respect to voltage $V_{FC}$ applied on front cathode 106. In an embodiment, $V_{FC}$ may be at ground potential, $V_{CA}$ may be at an intermediate voltage, and $V_{RA}$ may be at a high voltage. Electrical coupling 130 may supply front cathode 106 with a voltage $V_{FC}$, which may, in certain embodiments, be a ground potential. Center anode 108 and rear anode 110 may be instrumented to detect current pulses caused by the ionization of the gas as particles pass through the first detection chamber 102 and are stopped in the second detection chamber 104. These current pulses may be used to determine ΔE and E, respectively, of the particles.

I. General Operation

In basic operation, ionization detection chambers 102/104 may operate as ionization chambers, or proportional counters, depending, for example, on whether center anode 108 and/or rear anode 110 are constructed from a metalized film, such as aluminized Mylar, or a wire mesh or grid. Charged particles are accelerated, for example, by a Van de Graff accelerator. The particles are formed into a particle beam, for example, incident particle beam 120, with a trajectory that is coaxial with outer shell 112. In an embodiment of the invention, incident beam 120 travels through an evacuated tube, such as vacuum tube 114.

Incident beam 120 strikes a target material under test, for example, target 122, which may cause, for example, near-surface RBS backscattering and NRA nuclear reactions with the target material, depending on the composition and energy of the ion beam and the composition of the target. Backscattered ions and reaction products, such as alpha particles, beta particles, protons, etc., may generally be ejected from the target at all spherical angles. In an embodiment of the invention as illustrated, backscattered ions and reaction products that are ejected from the target 122 with an acute angle with respect to the incident particle beam 120, enter first detection chamber 102 through front cathode 106. This annular detector arrangement may have advantages over typical "point" detectors due to the relatively large solid detection angle that can be achieved by integrated ΔE-E annular detector 100. The time required to detect a sufficient quantity of reaction products may be much less than the time required for typical point detectors.

In various embodiments, front cathode 106 may be formed from an electrically conductive window, such as metalized Mylar film, that may be formulated or dimensioned, for example, to have a sufficient thickness such that backscattered ions from incident beam 120 are stopped and nuclear reaction products pass through the film, or to allow both backscattered ions from the incident beam 120 and nuclear reaction products pass through the film. For example, alpha particles with energy of 2 Million Electron Volts (2 MeV) have a range in Mylar of approximately 8.4 micrometers (μm). For these alpha particles to be detected by the ΔE detector, the front cathode 106 should have a thickness less than this. Various tools are available to assist in determining appropriate thicknesses for films. For example, the stopping distance of various ions in various materials as a function of the incident energy may be calculated using the SRIM program suite, developed Ziegler and Biersack. Nuclear reactions with positive Q values generally produce light particles with more energy than the primary incident beam. Thus, it may be easier for these particles to penetrate the front cathode 106 than heavier, less energetic particles from the beam.

Each chamber 102/104 is filled with an inert gas, such as Argon. If the chambers are operated as proportional counters, a quench gas, such as methane, is also added to the chambers at, for example, 10% by volume. Ionizing particles that enter first detection chamber 102 may collide with molecules of the inert gas and ionize it to produce an electron and a positively charged atom, known as an ion pair. As the charged particle travels through inert gas of the chamber, it leaves a trail of ion pairs along its trajectory.

In first detection chamber 102, the voltage differential between front cathode 106 and center anode 108 is strong enough to prevent recombination of the ion pairs and causes positive ions to drift towards front cathode 106 and electrons to drift towards center anode 108. Similarly, when the voltage applied to the rear anode 110 is larger than that applied to the center anode 108, the electrons produced by the ionization occurring in the second ionization chamber 104 drift towards the rear anode 110. When the detection chambers 102/104 are operated as ionization counters, the created ion pairs cause an ionization current to be collected on the center anode 108 and the rear anode 110, nearly simultaneously. The pulse amplitude at both the center anode 108 and the rear anode 110 is proportional to the energy loss of the backscattered beam or the reaction products as they traverse though the first detection chamber 102 and the second detection chamber 104, respectively, since the number of ion pairs created by the charged particle as the charged particle travels through inert gas of the chamber is proportional to the energy of the particles.

When the detection chambers 102/104 are operated as proportional counters, then in the immediate vicinity of the wires of the wire mesh or grid of center anode 108, or of rear anode 110, the electric field strength becomes large enough for the drifting electrons to produce Townsend avalanches. The quench gas acts to limit the magnitude and extent of the avalanche. The multiplication effect of the avalanche produced by each drifting electron of an ion pair allows for a better signal to noise ratio in detecting each ionizing event, and reduces the subsequent electronic amplification required. Each drifting electron of an ion pair produces only one avalanche. This provides proportionality between the number of original events and the total detected ion current. Thus, the energy of the backscattered or reaction product particle deposited in first detection chamber 102 is proportional to the number of original ionization events caused by the particle as it travels within, or traverses, first detection chamber 102, which in turn is proportional to the detected ion current.

In similar fashion, a backscattered or reaction product particle that enters second detection chamber 104 will also leave a trail of ion pairs along its trajectory, the number of which is proportional to the energy of the particle as it enters the second detection chamber. The voltage differential between rear anode 110 and center anode 108 is strong enough to prevent recombination of the ion pairs and causes electrons to drift towards rear anode 110. Similar to the operation of first detection chamber 102, the drifting electrons generate an ionization current pulse, which is then detected. The energy of the backscattered or reaction product particle deposited in second detection chamber 104 is proportional to the number of original ionization events caused by the particle as it travels within, or traverses, second detection chamber 104, which in turn is proportional to the detected ion current.

As described above, a $\Delta$E-E detector operates on the principle that a particle travels through a first $\Delta$E detector, in our case, first detection chamber 102, and is stopped in a second E detector, here; second detection chamber 104. The atomic number may be determined from the energy deposited by the particle within the thickness spanned by the $\Delta$E detector and the energy of the particle deposited in the E detector as the particle is brought to a stop within the E detector. The total particle energy is the sum of the detected energies deposited in the two detectors, plus the energy lost by the particle as it traverses the material of front cathode 106, for example, Mylar film, and center anode 108, for example, also Mylar film if detection chambers 102/104 are being operated as ionization counters.

Therefore, in various embodiments, the backscattered and reaction product particles of interest are those that are ejected from target 122 at a sufficiently acute angle so as to traverse the span of first detection chamber 102, and are stopped within second detection chamber 104, as illustrated by backscattered particle 124. These particles may be identified, for example, as those particles for which ion currents in both first and second detection chambers 102/104 are detected. In certain embodiments, recognizing that it may be preferable for such reaction product particles to deposit their remaining energy within the gas of second detection chamber 104 rather than striking the interior surface of outer shell 112, annular shielding, such as an adjustable iris placed before or within the $\Delta$E-E detector, may block reaction product particles that are ejected from target 122 that are not within a solid angle that allows for the particle trajectory to intersect rear anode 110, as illustrated by backscattered particle 126. Such an iris may also be used to limit the angular range subtended by the backscattered beam and reaction products. In addition, the iris might be useful to reduce the particle flux of the backscattered beam and reaction products striking the detector where the flux may be high enough to overwhelm the detection circuitry's ability to process individual events.

In embodiments of the invention, for each backscattered or reaction product particle that traverses the span of first detection chamber 102 and is stopped within second detection chamber 104, a $\Delta$E signal 132 and an E signal 134 are detected. These signals are representative of the ionization current detected on the center anode 108 and the rear anode 110, respectively.

Figure 2:
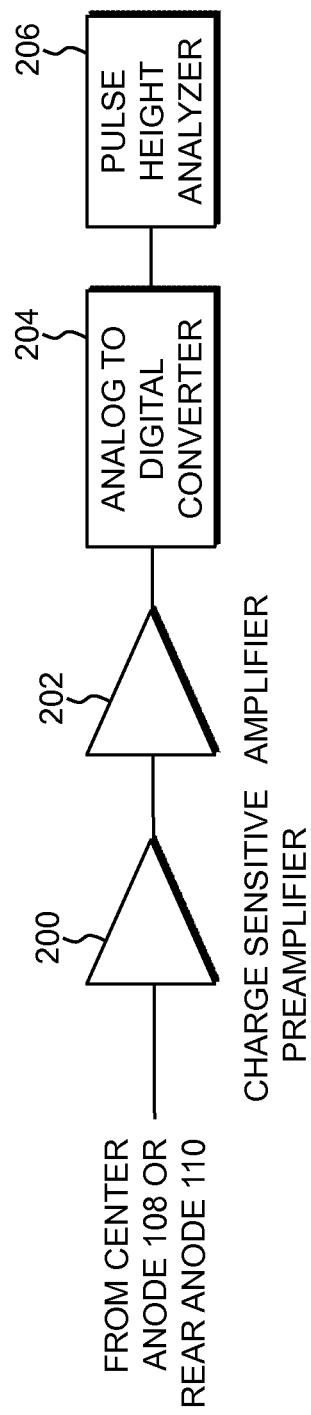
FIG. 2 illustrates a functional schematic diagram of an ionization or proportional counter circuit, in accordance with an embodiment of the invention.

FIG. 2 illustrates a functional schematic diagram of an ionization or proportional counter circuit, in accordance with an embodiment of the invention. In an embodiment, each of center anode 108 and rear anode 110 are coupled to an ionization or proportional counter circuit. A charge sensitive preamplifier 200 may be electrically coupled to center anode 108 or rear anode 110, and detect current pulses generated by the ionization currents. Preamplifier 200 generates a voltage output that is proportional to the current received, and is further amplified by an amplifier 202. The output of amplifier 202 is received by an analog-to-digital converter 204. The output signals from both analog to digital converter (204) are fed into a single pulse height analyzer 206. Logic signals gating the pulse height analyzer 206 enable the processing of the signal amplitudes originating from the center anode 108 and rear anode 110, only if signals of appropriate amplitude from the rear anode 110 are present. This ensures that events such as those depicted by backscattered particle 126 do not get processed.

As mentioned above, the reaction product particles of interest are those that are ejected from target 122 and traverse the span of first detection chamber 102, and are stopped within second detection chamber 104. These particles will produce a pair of signals in almost instantaneous succession—a $\Delta$E signal 132 and an E signal 134. To ensure that only corresponding pairs of signals are tracked, the pair of pulse analyzers may, for example, include filtering logic that stores a $\Delta$E-E signal pair only upon detection of both signals.

Generally, it is desirable for the $\Delta$E-E detector to produce energy profiles that have a high resolution for the backscattered and/or reaction product particles. That is, it is desirable to be able to statistically distinguish between the electrical signals produced by different particles that may have similar energies. As mentioned above, several physical aspects of a $\Delta$E-E detector, in accordance with various embodiments, may be adjustable. These physical aspects may be advantageously adjusted to improve the energy resolution of the $\Delta$E-E detector, based on, for example, the thickness of the Mylar films of front cathode 106 and center anode 108, the gas pressures within first and second detection chambers 102/104, the spacing between the center anode 108 and the front cathode 106, the spacing between the rear anode 110 and the center anode 108, and perhaps the incident beam energy. For example, it is known that a greater gas pressure, and hence greater gas density, within a gas ionization detector results in a greater likelihood of collisions of the ionizing particles with the gas, and therefore a greater rate of ion pair generation and energy loss of the particle. It is also known that increasing the path length that an ionizing particle traverses within a gas ionization detector, all other parameters remaining the same, results in a greater likelihood of collisions of the ionizing particles with the gas and energy loss of the particle. Depending on the energy and composition of the incident particle beam 120 and the composition of the target material 122, the gas pressures within first and second detection chambers 102/104 and or the axial separation of front cathode 106, center anode 108, and rear anode 110 may be adjusted to optimize, for example, the energy resolution information of the $\Delta$E-E detector.

II. Exemplary Embodiments

In various exemplary embodiments, the front cathode 106, the center anode 108, and rear anode 110 are constructed from aluminized Mylar film with a thickness of approximately 1-15 μm. The cathode and anode film may have a diameter of approximately 10-100 mm. While exemplary embodiments are described as having Mylar film cathodes and anodes, any film or substance that operates in accordance with one or more embodiments of the invention may be used. In general, the film or substance must be electrically conductive or support a coating that is electrically conductive, be thin enough to allow ion beam backscattered and nuclear reaction product particles of interest to pass through with minimal energy loss, but thick enough to support a desired pressure differential, usually between 0-760 T, and more typically between 100-500 T. In an embodiment, the thickness of the aluminized Mylar film on the front cathode 106 may be chosen to stop the backscattered beam, but made thin enough to allow the passage of the energetic reaction products. For example, using NRA with a deuterium beam of approximately 1 MeV incident energy, a Mylar film of about 14 um would stop the beam but allow the energetic reaction products—protons in the case of a target 122 containing $^{16}O$ or $^{12}C$, or alpha particles in the case of a target 122 containing $^{14}N$—to pass through.

FIGS. 3A-3B illustrate an exemplary embodiment of a cathode and/or anode structure, in accordance with an embodiment of the invention. FIG. 3A is a front planar view of a cathode and/or anode structure, in accordance with an embodiment of the invention. An aluminized Mylar film 302 is attached to a frame 300 so as to form a hermetic seal. For example, frame 300 may be formed of two circumferential pieces, between which is held Mylar film 302. For example, the two circumferential pieces may be aligned and glued to either side of Mylar film 302. An arrangement of spokes 304 may provide additional structural support to Mylar film 302, and provide structural support for center hub 306. In various embodiments, it is desirable to minimize the axial profile of spokes 304 so as to minimize the amount of particles blocked by the spokes, but allow for sufficient structure to support Mylar film 302 at the expected pressure differentials. For example, the spokes may have a blocking profile of 10% or less of Mylar film 302 for particle trajectories that pass through the film.

FIG. 3B is a perspective view of the exemplary cathode and/or anode structure of FIG. 3A. As illustrated, spokes 304 have an axial dimension that may be approximately the axial width of frame 300. Similar to frame 300, spokes 304 and hub 306 may be formed of two circumferential pieces may be aligned and glued to either side of Mylar film 302. A hermetic seal, at least, must be present between Mylar film 302 and hub 306.

As described above, an aspect of one exemplary embodiment is the ability of the cathode 106 and anodes 108 and 110 to independently move axially within an outer shell. As illustrated, this may be accomplished through the use of O-rings 308 disposed circumferentially about the outer surface of frame 300. FIG. 3C illustrates a partial sectional view of an outer portion of frame 300 that includes double O-rings 308. Frame 300, O-rings 308, and the outer shell 112 may be dimensioned to allow a sufficient compression fit such that frame 300 may move axially within the outer shell 112 as desired, and a hermetic seal is maintained by the O-rings. Similarly, although not illustrated in FIGS. 3A-3B, O-rings may be disposed circumferentially about the inner surface of hub 306 such that a hermetic seal is maintained with, for example, axial vacuum tube 114, and the anode or cathode may be axially moved as desired. In one embodiment, a suitable grease may be used to aid in providing the hermetic seal between the O-rings and the outer shell or vacuum tube, and assist in allowing axial movement of the cathode and anodes in the outer shell and along the center vacuum tube.

Alternative embodiments to the frame, hub, and spoke structure supporting a Mylar film cathode or anode, as illustrated in FIGS. 3A-3B, may include using a wire mesh or grid for the center anode 108 and rear anode 110. In these embodiments, because there will be no gas pressure differential between the two detection chambers, and a hermetic seal between either of the anodes to the outer support frame and inner hub is not needed, a less robust support structure may be used. In other embodiments, a lightly supported very thin Mylar film may be used as a center anode if the pressure differential between the two detection chambers is kept at a minimum. This embodiment may have the advantage of low energy loss as particles traverse the anode material. Those skilled in the art will recognize that other embodiments may be used. For example, if rear anode 110 is implemented as a wire mesh or grid, a cap, such as a Mylar film, may be required to hermetically seal the rear of outer shell 112.

Figure 4:
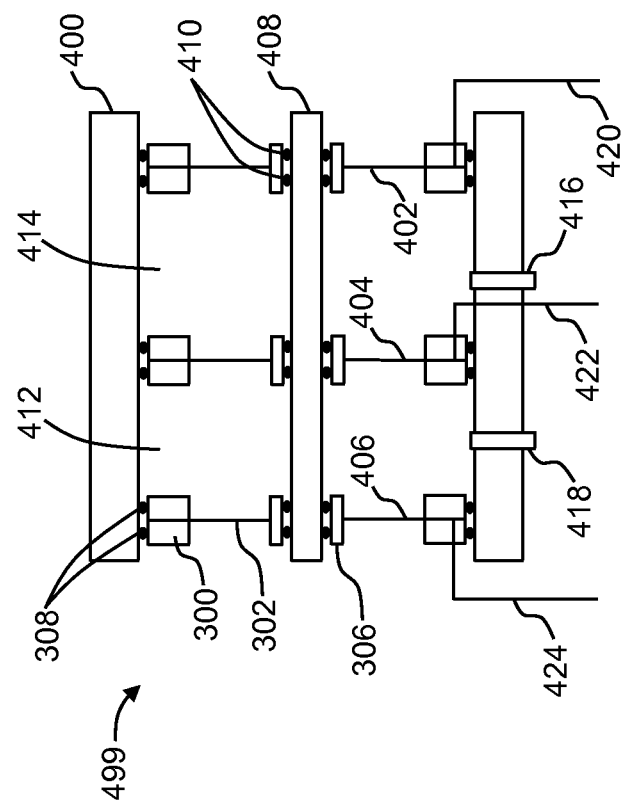
FIG. 4 is a center plane sectional view of a ΔE-E annular gas ionization detector, in accordance with an embodiment of the invention.

FIG. 4 is a center plane sectional view of a ΔE-E annular gas ionization detector 499, in accordance with an embodiment of the invention. ΔE-E annular gas ionization detector 499 includes outer shell 400, front cathode 402, center anode 404, rear anode 406, and vacuum tube 408. Front cathode 402, center anode 404, and rear anode 406 are formed as described in relation to FIGS. 3A-3C above. Each includes an outer frame 300 and inner hub 306 that support, for example, an aluminized Mylar film cathode or anode 302. Not shown are spoke support structures between outer frame 300 and inner hub 306 that may be present. O-rings 308 are disposed between outer frame 300 and outer shell 400. Similarly, O-rings 410 are disposed between inner hub 306 and vacuum tube 408. Outer shell 400, as illustrated, includes a gas port 416 for first detection chamber 414, and a gas port 418 for second detection chamber 412. Electrical coupling 420 may supply front cathode 402 with a voltage $V_{FC}$, which may, in certain embodiments, be a ground potential. Electrical couplings 422 and 424 may connect the center anode 404 and rear anode 406 to external current pulse detection circuitry, such as illustrated in FIG. 2, and may supply voltages $V_{CA}$ and $V_{RA}$, respectively.

In exemplary embodiments, outer shell 400, vacuum tube 408, outer frames 300, and inner hubs 306 may be formed of copper. Cathode 402, and anodes 404 and 406 are electrically isolated from outer shell 400. In various embodiments, O-rings 308 and 410 may assist in electrically isolating the cathodes and anode from the outer shell. In certain embodiments, cathode 402 may be electrically connected to outer shell 400. In various embodiments, detector 499 may be disposed within a grounded "can," and outer shell 400, cathode 402, and anodes 404 and 406 may be at electrical potentials other than ground. In an embodiment, outer shell 400 may be of an electrically insulating material.

It is noted that various geometries and arrangements may reduce the efficiency and accuracy of detector 499 by generating electrical fields that direct the electrons from the ionization pairs onto trajectories that do not strike an anode. For example, in an arrangement where the outer shell 400 is grounded, the electric fields within detector 499 may direct electrons of the ionization pairs to the grounded shell, thus reducing or eliminating the ionization current for the associated ionizing particle. Those skilled in the art will recognize alternate embodiments whereby the inner wall of outer shell 400 could be lined with a voltage divider network in region 414 spanning the voltage from the front cathode 106 to the center anode 108, and in region 412 spanning the voltage between the rear anode 110 and the center anode 108.

Figure 5:
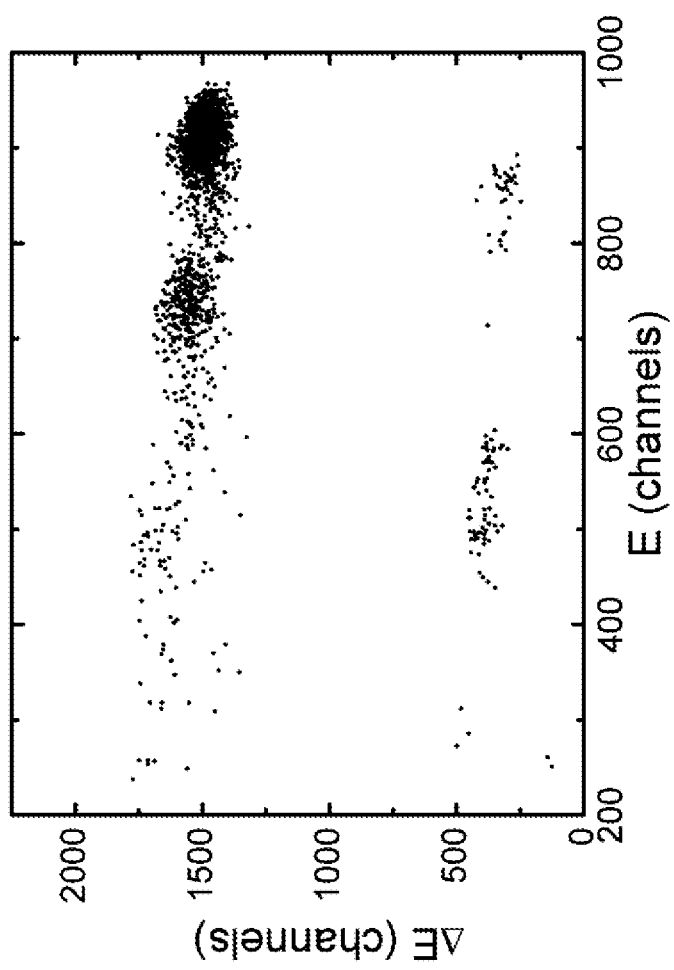
FIG. 5 represents an exemplary ΔE-E plot of detected energies from backscattered ion beam and reaction product particles resulting from the interactions of an ion beam and a target, in accordance with an embodiment of the invention.

FIG. 5 represents an exemplary ΔE-E plot of detected energies from the backscattered ion beam and reaction product particles resulting, for example, from the interactions of an ion beam 120 and a target 122, in accordance with an embodiment of the invention. Each plotted point represents the detected $\Delta E$ and E energies of a backscattered or reaction product particle. As illustrated, there are two groupings of plotted points—a first grouping at higher $\Delta E$ energies representing detected energies of the backscattered ion beam, and a second grouping at lower $\Delta E$ energies representing detected energies of the nuclear reaction products.

The descriptions of the various embodiments of the present invention have been presented for purposes of illustration, and are not intended to be exhaustive or limited to the embodiments disclosed. Many modifications and variations may be apparent to those of ordinary skill in the art without departing from the scope and spirit of the invention. Therefore, the present invention has been disclosed by way of example and not limitation. The terminology used herein was chosen to best explain the principles of the one or more embodiments, the practical applications or technical improvements over technologies found in the marketplace, or to enable others of ordinary skill in the art to understand the embodiments disclosed herein.

What is claimed is:

1. An integrated $\Delta E$-E ionization detector, comprising:
an outer shell having an interior linear axis;
a vacuum tube coaxial with the linear axis;
a front cathode, a center anode, and a rear anode disposed within the outer shell and around the vacuum tube;
wherein the front cathode, center anode, and rear anode are substantially planar in shape;
wherein a $\Delta E$ detection chamber is defined by the front cathode, the center anode, the outer shell, and the vacuum tube, and an E detection chamber is defined by the rear anode, the center anode, the outer shell, and the vacuum tube; and
wherein all rays defining at least one solid annular angle about the linear axis and originating from a point in front of the front cathode will intersect the front cathode, internally traverse the $\Delta E$ detection chamber, intersect the center anode, and traverse at least a portion of the E detection chamber.

2. An integrated $\Delta E$-E ionization detector in accordance with claim 1, wherein the front cathode, center anode, and rear anode are substantially parallel to each other, and are substantially orthogonal to the linear axis.

3. An integrated $\Delta E$-E ionization detector in accordance with claim 1, wherein the front cathode, center anode, and rear anode are formed of electrically conductive, non-gas permeable film, and the $\Delta E$ detection chamber and the E detection chamber are each hermetically sealed.

4. An integrated $\Delta E$-E ionization detector in accordance with claim 3, wherein the outer shell includes a gas port into the $\Delta E$ detection chamber and a gas port into the E detection chamber, whereby the gases in the $\Delta E$ detection chamber and the E detection chamber may be maintained at different pressures.

5. An integrated $\Delta E$-E ionization detector in accordance with claim 1, wherein the front cathode is formed of electrically conductive, non-gas permeable film, the center and rear anodes are formed of a wire mesh or grid, and the combined $\Delta E$ detection chamber and E detection chamber is hermetically sealed.

6. An integrated $\Delta E$-E ionization detector in accordance with claim 1, wherein each of the front cathode, center cathode, and rear cathode are formed of one of an electrically conductive, non-gas permeable film, and a wire mesh or grid, and the combined $\Delta E$ detection chamber and E detection chamber is hermetically sealed.

7. An integrated $\Delta E$-E ionization detector in accordance with claim 1, wherein the outer shell is cylindrical.

8. An integrated $\Delta E$-E ionization detector in accordance with claim 1, wherein the outer shell is frusto-conical.

9. An integrated $\Delta E$-E ionization detector in accordance with claim 1, wherein the outer shell is formed of a frustum.

10. An integrated $\Delta E$-E ionization detector in accordance with claim 1, wherein the front cathode, center anode, and rear anode are independently axially moveable within the outer shell.

11. An integrated $\Delta E$-E ionization detector in accordance with claim 1, furthering comprising an iris operated to block a portion of the particle flux of a backscattered beam and reaction products from striking the detector.

* * * * *